United States Patent [19]

Myers et al.

[11] Patent Number: 5,113,033
[45] Date of Patent: May 12, 1992

[54] RUTHENIUM SALT AND ALUMINUM HALIDE CATALYST SYSTEM FOR CODIMERIZATION OF ALPHA MONOOLEFINS AND CONJUGATED DIOLEFINS

[75] Inventors: Richard S. Myers, Kutztown, Pa.; Daniel R. Mills, Somerville; Robert C. Michaelson, Kinnelon, both of N.J.

[73] Assignee: Exxon Chemical Patents Inc., Linden, N.J.

[21] Appl. No.: 464,088

[22] Filed: Jan. 12, 1990

[51] Int. Cl.$^5$ ................................................. C07C 2/02
[52] U.S. Cl. ..................................... 585/506; 585/601
[58] Field of Search ............................... 585/506, 601

[56] References Cited

U.S. PATENT DOCUMENTS

| 3,013,066 | 12/1961 | Alderson . | |
| 3,131,155 | 4/1964 | Luttinger | 585/506 |
| 3,361,840 | 2/1968 | Kohll et al. . | |
| 3,523,983 | 8/1970 | Gough . | |
| 3,546,083 | 12/1970 | Ort et al. . | |
| 3,636,122 | 1/1972 | Cramer et al. | 585/506 |
| 3,640,898 | 2/1972 | Su . | |
| 3,742,080 | 1/1973 | Su | 585/506 |

FOREIGN PATENT DOCUMENTS

| 691770 | 8/1964 | Canada . |
| 2050774 | 4/1971 | Fed. Rep. of Germany . |
| 2240719 | 3/1973 | Fed. Rep. of Germany . |

*Primary Examiner*—Patrick P. Garvin
*Assistant Examiner*—F. D. Irzinski
*Attorney, Agent, or Firm*—Edward F. Sherer

[57] ABSTRACT

A catalyst system for codimerization of alpha-monoolefins and conjugated diolefins to yield 1,4-dienes. The catalyst system includes at least one ruthenium salt and at least one aluminum halide. Suitable aluminum halides include both alkyl aluminum halides and nonalkylated aluminum halides, as well as mixtures thereof.

45 Claims, No Drawings

RUTHENIUM SALT AND ALUMINUM HALIDE CATALYST SYSTEM FOR CODIMERIZATION OF ALPHA MONOOLEFINS AND CONJUGATED DIOLEFINS

BACKGROUND OF THE INVENTION

1. Field of the Invention

This invention relates to catalyst systems including ruthenium salts and aluminum halides; the aluminum halides include both nonalkylated and alkyl aluminum halides. These catalyst systems are employed in the codimerization of alpha-monoolefins and conjugated diolefins to yield 1,4-dienes.

2. Description of Material Information

Nonconjugated diolefins, including the 1,4-dienes, can be employed for a variety of purposes. The trans-isomers of 1,4-dienes are useful as polymerization starting materials; cis-1,4-dienes, however, impact unfavorably on the desired reaction.

As a particular example, trans-1,4-hexadiene is useful in the production of functionalizable polymers, and is employed in preparing EPDM terpolymer. Cis-1,4-hexadine, however, has a deleterious effect on polymerization catalysts, and, moreover, is difficult to separate from trans-isomer.

1,4-dienes can be obtained from codimerization of alpha-monoolefins and conjugated dienes; specifically, 1,4-hexadiene is yielded from ethylene and 1,3-butadiene. Because of the desirability of the trans-isomers and the undesirability of cis-isomers, codimerizations selective for the former are preferred; the less cis-isomer produced relative to trans-isomer, the more desirable the reaction.

The requisite codimerization may be carried out by a variety of methods, including anionic, cationic, and transition metal-catalyzed processes. Of particular relevance are codimerizations conducted in the presence of soluble transition metal salts; a variety of such processes are known in the art.

Codimerization catalyst systems utilizing different Group VIII metals, including systems which are selective to the trans-isomer, are known. U.S. Pat. Nos. 3,640,898 and 3,742,080 both disclose a catalyst system yielding 1,4- dienes in high trans to cis ratio, comprising a rhodium (III) salt and at least one promoter selected from amides, phosphoramides, phosphine oxides, and water. However, the high cost of rhodium makes such catalyst systems undesirable.

Catalyst systems particularly utilizing ruthenium compounds are also known. U.S. Pat. No. 3,523,983 discloses a catalyst system comprising a ruthenium salt, dissolved in a hydrocarbon solvent, incorporating a proportion of water, hydrogen, or hydride, such as alkali metal aluminum hydride. U.S. Pat. No. 3,361,840 discloses a salt of a Group VIII metal, such as ruthenium, and an organic nitro compound in substantially anhydrous liquid medium. Canadian Patent No. 691,770 discloses solutions of Group VIII noble metal salts, including various specified ruthenium salts, as dimerization catalyst systems. However, none of these references discloses or suggests either the presence of an alkyl aluminum halide in conjunction with the ruthenium salt component of the catalyst system, or the use of the catalyst system for the synthesis of 1,4-dienes.

It has been discovered that catalyst systems incorporating both ruthenium salts and aluminum halides, including the alkyl aluminum halides as well as the nonalkylated aluminum halides, are characterized by both high activity and high trans-selectivity in the codimerization of alpha-monoolefins and conjugated dienes. Particularly as to the codimerization of ethylene and 1,3-butadiene, selectivities as high as 20:1 trans to cis, and higher, may be achieved.

SUMMARY OF THE INVENTION

This invention concerns a process for the synthesis of 1,4-dienes from alpha-monoolefins and conjugated dienes, a catalyst system for the codimerization process of the invention, and a process for the preparation of the catalyst system.

The catalyst system of the invention comprises a catalyst and a co-catalyst. The catalyst is a ruthenium compound—more specifically, a ruthenium salt; the co-catalyst is an aluminum halide. One or more of each of the ruthenium compound and the aluminum halide may be included.

Suitable ruthenium salts for the catalyst system of the invention include ruthenium(III) salts, and salts which can be converted to the $+3$ oxidation state. Particular ruthenium (III) salts include the halides, such as $RuBr_3$, $RuCl_3$, $RuI_3$, as well as the hydrate of each, i.e., $RuBr_3.XH_2O$, $RuCl_3.XH_2O$, and $RuI_3.XH_2O$.. Also included are $Ru(acetylacetonate)_3$, $Ru(hexafluoroacetylacetonate)_3$, $Ru(benzoylacetonate)_3$, $RuCl_3(NH_3)_5$, $RuCl_3(NH_3)_6$, $RuCl_3NO$, $(NH_4)_2[RuCl_5]$, $K_2[RuCl_5]$, $RuNO(NO_3)_3$, and $K_3Ru(C_2O_4)_3$. Of the particular ruthenium (III) salts listed above, ruthenium (acetylacetonate)$_3$ and $RuCl_3X-H_2O$ are preferred.

Suitable aluminum halides include alkyl aluminum halides and nonalkylated aluminum halides. The alkyl aluminum halides, which are both alkylating agents and Lewis acids, are particularly preferred.

The preferred alkyl aluminum halides are those having the general formula $RAlXZ$, with R being a $C_1$–$C_{10}$ hydrocarbon, and X being a halogen. F, Cl, Br and I are suitable such halogens. R and X may be mixtures of such $C_1$–$C_{10}$ hydrocarbons and halogens, respectively. Z is any of the hydrocarbons which may be R, any of the halogens which may be X, or a mixture thereof.

Specific alkyl aluminum halides which are suitable for the catalyst system of the invention include methyl aluminum dichloride, methyl aluminum dibromide, ethyl aluminum dichloride, ethyl aluminum dibromide, ethyl aluminum diiodide, dimethyl aluminum chloride, dimethyl aluminum bromide, diethyl aluminum chloride, diethyl aluminum bromide, di-n-propyl aluminum chloride, and di-n-propyl aluminum bromide, diisobutyl aluminum chloride, and diisobutyl aluminum bromide. Mixtures and addition compounds of such alkyl aluminum halides are also suitable; specific such addition compounds include ethyl aluminum sesquichloride and methyl aluminum sesquichloride.

The nonalkylated aluminum halides, which are Lewis acids but not also alkylating agents, are also suitable as catalysts. Aluminum chloride, aluminum bromide, aluminum iodide, and aluminum fluoride are all appropriate co-catalysts for the catalyst system of the invention.

A plurality of aluminum halides may be employed, in any combination which will facilitate the requisite dimerization. Specifically, a plurality of alkyl aluminum halides, or a plurality of nonalkylated aluminum halides, are both appropriate. Also suitable is a combination including one or more alkyl aluminum halides and one or more nonalkyl aluminum halides.

The ruthenium salt catalyst and aluminum halide co-catalyst may be present in any relative proportions which provide for operability of the catalyst system; the catalyst system has utility when both the catalyst and the co-catalyst are present in equimolar amounts, as well as when the proportion of one is greater of that of the other.

In a preferred embodiment of the catalyst system of the invention, the relative proportions of ruthenium salt and aluminum halide are such that the molar ratio of aluminum halide to ruthenium salt is about 1:1 or greater. In a particularly preferred embodiment, the molar ratio of aluminum halide to ruthenium salt is between about 1:1 and about 4:1; where the aluminum halide is an alkyl aluminum halide, the amount of alkyl aluminum halide in this proportion is expressed as mole of available hydrocarbon moiety.

The catalyst system of the invention may also include a solvent for the ruthenium catalyst and the aluminum halide co-catalyst. Preferably, the boiling point of this solvent is higher than that of the reaction products resulting from a codimerization reaction utilizing the catalyst system of the invention. The solvent is also preferably a weakly coordinating solvent; particular such solvents include diethyl ether, dibutyl ether, acetonitrile, and tetrahydrofuran.

Particularly preferred weakly coordinating solvents for the catalyst system of the invention are the glymes, i.e., ethers having the formula

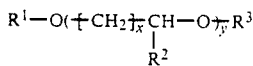

wherein:

$R^1$ is an alkyl group having at least one carbon atom;
$R^2$ is a hydrogen or an alkyl group having at least one carbon atom;
$R^3$ is an alkyl group having at least one carbon atom, and may be the same as, or different from, $R^1$;
x is 0 or greater; and
y is 1 or greater.

Particularly preferred solvents of this formula are ethylene glycol dimethyl ether and its higher homologs.

Noncoordinating solvents, such as hydrocarbon solvents, may also be used. A particular suitable noncoordinating solvent is toluene.

Where the solvent is a noncoordinating solvent, the catalyst system of the invention preferably includes a coordinating ligand, included either as a part of the ruthenium catalyst, or added to the system independently. A particular combination having utility are toluene and triphenyl phosphine, as the solvent and independently added coordinating ligand, respectively.

Ruthenium salts which can be converted to the $+3$ oxidation state are also suitable for the catalyst system of the invention. Among such ruthenium salts are those which, prior to conversion, have an oxidation state greater than $+3$; particular examples include $RuO_4$, $NaRuCl_5$, $NaRuBr_5$, $(NH_4)_2RuCl_6$, $KRuO_4$, $K_2RuO_4$, $NaRuO_4$, and $RuO_2$.

Yet additional ruthenium salts suitable for the catalyst system of the invention are those which have been converted to the $+3$ oxidation state, from a ruthenium salt having an oxidation state less than $+3$. Specific examples of suitable ruthenium salts having an oxidation state less than $+3$ include $K_4[Ru(CN)_6]$, $K_2[Ru(CO)_2Cl_4]$, $K[Ru(CO)_3Cl_3]$, $Ru(H_2NCH_2CH_2NH_2)_3Cl_2$, $Ru(P\phi_3)_2(CO)_2Cl_2$, $Ru(P\phi_3)_2(CO)_3$, $Ru(P\phi_3)_3Cl_2$, $Ru(NH_3)_3Cl_2$, $HRu(P\phi_3)_3(CO)Cl$, $H_2Ru(P\phi_3)_3(CO)$, $HRu(P\phi_3)_3Cl$, $H_2Ru(P\phi_3)_4$, $Ru(NH_3)_6Cl_2$, and $Ru_3(CO)_{12}$.

The codimerization process of the invention pertains to preparation of a 1,4-diene from an alpha-monoolefin and a conjugated diolefin. The alpha-monoolefin and conjugated diolefin are subjected to codimerization in the presence of a catalyst system of the invention, as previously discussed.

The process of the invention may utilize a ruthenium salt having an oxidation state greater than $+3$. Such an embodiment entails reducing such a ruthenium salt to the $+3$ oxidation state, forming a catalyst system comprising the reduced ruthenium salt and an aluminum halide, as previously discussed, and reacting an alpha-monoolefin and a conjugated diolefin in the presence of this catalyst system.

As one alternative, reduction of the ruthenium salt may be effected as a step separate from, and prior to, formation of the catalyst system, by means of reaction with a suitable reducing agent. Alternatively, ruthenium salt having an oxidation state greater the $+3$ may be combined with the aluminum halide co-catalyst, or added to the dimerization reaction, in the unreduced state; in such instance, reduction to the requisite $+3$ oxidation state occurs in situ.

The dimerization process of the invention can also be conducted with a ruthenium salt convertible to the $+3$ oxidation state, as previously discussed, which has an oxidation state less than $+3$ prior to the requisite conversion. In this embodiment, the ruthenium salt is initially raised to the requisite $+3$ oxidation state; one means for so raising the oxidation state of the ruthenium salt is by reaction with a suitable oxidizing agent. Thereafter, a catalyst system incorporating the ruthenium salt and an aluminum halide is formed; an alpha-monoolefin and a conjugated diolefin are reacted in the presence of this catalyst system to yield a 1,4-diene.

The invention further pertains to a process for preparing a catalyst system. One embodiment of this process, utilizing a ruthenium salt having an oxidation state greater than $+3$, comprises reducing this ruthenium salt to the $+3$ oxidation state; thereafter, both this reduced ruthenium salt and an aluminum halide, as previously discussed, are dissolved in a solvent.

Suitable such ruthenium salts, having an oxidation state greater $+3$ prior to conversion, include those salts of this type as previously mentioned. The reduction step may be accomplished by reacting the ruthenium salt with a reducing agent.

Another embodiment of the process for preparing the catalyst system of the invention utilizes a ruthenium salt having an oxidation state less than $+3$. In this embodiment, the ruthenium salt is oxidized to the $+3$ oxidation state, and then dissolved, with an aluminum halide as previously discussed, in a solvent.

A suitable means for oxidizing the ruthenium salt in this embodiment is by reaction with an oxidizing agent. Appropriate such ruthenium salts include those having an oxidation state less than $+3$, as previously discussed.

Appropriate solvents for use in the catalyst system preparation process of the invention include those solvents as previously discussed. Weakly coordinating ether solvents are preferred.

DESCRIPTION OF PREFERRED EMBODIMENTS

With regard to the composition of the ruthenium (III) halide hydrates, the number of water molecules associated with each ruthenium (III) halide molecule is variable. Accordingly, as set forth herein, the formulae for these hydrates identifies the water component as "$XH_2O$", e.g., $RuBr_3 \cdot XH_2O$, with X representing the number of water molecules.

1,4-dienes, as referred to herein, are nonconjugated diolefins, and include the structure —C=C—C—C=C—; examples of 1,4-dienes are 1,4-hexadiene and 2,5-heptadiene. The symbol $\phi$, as used herein, refers to phenyl, i.e., $C_6H_5$.

Also as referred to herein, the aluminum halides include both the alkylated aluminum halides and the nonalkylated aluminum halides. The alkyl aluminum halides are understood as being aluminum halides provided with a hydrocarbon, e.g., alkyl, moiety; they serve both as alkylating agents and as Lewis acids. The nonalkylated aluminum halides are aluminum halides without alkyl substituents, and include $AlCl_3$, $AlBr_3$, $AlI_3$, and $AlF_3$; these act as Lewis acids, but not also as alkylating agents.

The alpha-monoolefins employed in the process of the invention have the formula:

$$R-CH=CH_2$$

wherein R is hydrogen, $C_1$-$C_{16}$ alkyl, or halogenated $C_1$-$C_{16}$ alkyl. The preferred alpha-monoolefins are those having up to about 6 carbon atoms.

The most preferred alpha-monoolefin is ethylene, which is available in large quantities at a low price, and readily combines with conjugated dienes to give important 1,4- dienes. Ethylene is particularly significant as being codimerizable with 1,3-butadiene to yield 1,4-hexadiene.

Propylene is also preferred because of its availability, and the importance of the 1,4-dienes prepared from it. Other examples of suitable alpha-monoolefins for the codimerization process of the invention are set forth in NYCE et al., U.S. Pat. No. 3,222,330.

The conjugated dienes suitable for codimerization with the alpha-monoolefins previously discussed have the formula:

$$(R)_2C=CH-CH=C(R)_2$$

wherein R is hydrogen, $C_1$-$C_{15}$ alkyl, $C_7$-$C_{18}$ alkaryl, $C_7$-$C_{18}$ aralkyl, or $C_6$-$C_{25}$ aryl. R can also be substituted with halogen or alkoxy groups. The preferred conjugated diolefin is 1,3-butadiene.

One or more of such alpha-monoolefins, and/or one or more of such conjugated diolefins, may be used in the codimerization reaction of the invention. Particular additional codimerization reactions include the reaction of ethylene and 1,3-pentadiene to provide 2,5-heptadiene, and the reaction of propylene and isoprene, which results in a mixture including four geometrical $C_8$ 1,4-diene isomers (i.e., 2-methyl-2,5-heptadiene; 2,5-dimethyl-1,4-hexadiene; 3-methyl-2,5-heptadiene; 2,4-dimethyl-1,4-hexadiene); these are provided only as representative samples, without limiting the combinations of alpha-monoolefin and conjugated diolefin reactants, and 1,4-diene products.

The codimerization reaction to form the 1,4-diene is an equimolar addition of alpha-monoolefin and conjugated diolefin. However, the relative proportions of reactants actually present can vary widely; an excess of either, as well as equimolar amounts, is within the scope of the invention. For example, in typical batch operations, the ratio of reactants can be continually changing, as discussed hereinafter; in any given reaction, the proportion of reactants used can be routinely determined by one skilled in the art.

The catalyst system of the invention includes, as the catalyst, a ruthenium compound, and an aluminum halide co-catalyst. One or more of each or both of the catalyst and the co-catalyst may be employed.

Ruthenium compounds suitable for the catalyst system of the invention include ruthenium salts, particularly those which are soluble in the dimerization solvent and dimerization reaction mixture, or which can be converted to a soluble ruthenium species under the conditions for conducting the dimerization reaction of the invention. Among the appropriate ruthenium salts are ruthenium (III) salts, and ruthenium salts convertible to the +3 oxidation state, including those so convertible under the indicated dimerization reaction conditions.

The ruthenium (III) salts include those having the general formula $RuX_3$. X may be an uninegative ligand; examples include hydrides, halides, pseudohalides, cyanides, carboxylic acids, etc. X may also be selected from the bidentate univalent ligands, such as acetylacetonate, hexafluoroacetylacetonate, benzoylacetonate, and derivatives thereof.

Specific examples of Ruthenium (III) salts are $RuBr_3$, $RuCl_3$, $RuI_3$, well the hydrates of each of these halides $Ru(acetylacetonate)_3$, $Ru(hexafluoroacetylacetonate)_3$, $Ru(benzoylacetonate)_3$, $RuCl_3(NH_3)_6$, $RuCl_3(NH_3)_6$, $RuCl_3NO$, $(NH_4)_2[RuCl_5]$, $K_2[RuCl_5]$, $RuNO(NO_3)_3$, and $K_3Ru(C_2O_4)_3$.

The ruthenium salts convertible to the +3 oxidation state include those which, prior to conversion, have an oxidation state greater than +3. Suitable such compounds are those convertible during the dimerization reaction. Specific examples are $RuO_4$, $NaRuCl_5$, $NaRuBr_5$, $(NH_4)_2RuCl_6$, $KRuO_4$, $K_2RuO_4$, $NaRuO_4$, and $RuO_2$.

The indicated ruthenium salts, having an oxidation state greater than +3, can be converted to the +3 oxidation state by reduction.

In the reaction mixture for synthesizing 1,4-dienes, both the aluminum halide and the olefins subjected to dimerization act as reducing agents. Accordingly, ruthenium salts of such greater oxidation state can be employed in the dimerization reaction without requiring prior reduction to the +3 oxidation state; such salts will be reduced in situ to the necessary +3 oxidation state for catalysis of the dimerization reaction.

Alternatively, these salts may be subjected to reduction prior to incorporation in the catalyst system of the invention. Conventional reducing agents, such as olefins, alcohols, and halides may be used; specific examples include ethanol, isobutanol, ethylene, and propylene, as well as iodides and bromides in general, i.e., those compounds which will provide iodide and bromide ions in solution. The reduction reaction may be conducted by any conventional means, such as in a slip stream reactor.

The convertible ruthenium salts also include those having, prior to conversion, an oxidation state less than +3. Specific examples are $K_4[Ru(CN)_6]$, $K_2[Ru(CO)_2Cl_4]$, $K[Ru(CO)_3Cl_3]$, $Ru(H_2NCH_2CH_2NH_2)_3Cl_2$, $Ru(P\phi_3)_2(CO)_2Cl_2$, $Ru(P\phi_3)_2(Co)_3$, $Ru(P\phi_3)_3Cl_2$, Ru(NH₃)₃Cl₂, HRu(Pϕ₃)₃(CO)Cl, H₂Ru(Pϕ₃)₃(CO), HRu(Pϕ₃)₃Cl, H₂Ru(Pϕ₃)₄, Ru(NH₃)₆Cl₂, and Ru₃(CO)₁₂.

Convertible ruthenium salts having an oxidation state less than +3 must be converted to the +3 oxidation state by oxidation, prior to incorporation in the catalyst system of the invention. Conventional oxidizing agents, including air, Cl₂, HOCl, and H₂O₂, are suitable for the oxidation reaction, which may be conducted by any conventional means; as with the previously discussed reduction reaction, a slip stream reactor is also appropriate for this oxidation reaction.

Neutral coordinating ligands, such as nitriles, phosphines, carbonyls, arsines, stibines, and mixtures thereof, may additionally be present in the catalyst system of the invention. Suitable phosphines, arsines, and stibines include those of the general formulae $(R^4)_3P$ and $(R^4)_3PO$, $(R^4)_3As$, and $(R^4)_3Sb$, respectively, where $R^4$ is a hydrocarbon moiety, such as methyl, ethyl, propyl, n-butyl, isobutyl, t-butyl, phenyl, etc. Among the specific eligible phosphines are triethyl phosphine and tri-n-butyl phosphine oxide.

These ligands may be introduced into the catalyst system of the invention as part of the ruthenium catalyst. Alternatively, neutral coordinating ligands may be added independently from the ruthenium catalyst; incorporated in this manner, the ligand will coordinate with the ruthenium salt in situ.

Among the aluminum halides which may be employed in the catalyst system of the invention are the alkylated aluminum halides, which act both as alkylating agents and Lewis acids, and the nonalkylated aluminum halides, which also act as Lewis acids, but not as alkylating agents. A single aluminum halide, or a plurality of aluminum halides, may be employed in the catalyst system of the invention, in any combination which will render this system capable of catalyzing the desired dimerization reaction.

Appropriate combinations include one or more alkyl aluminum halides, and one or more nonalkylated aluminum halides, as well as combinations of each of one or more alkyl aluminum halides and one or more nonalkylated aluminum halides. A particular combination having utility is ethyl aluminum sesquichloride and aluminum chloride.

Suitable alkyl aluminum halides for the catalyst system of the invention are those having the formula:

RAlXZ

R is a $C_1$-$C_{10}$ hydrocarbon moiety. Included among suitable R groups are normal, iso-, and tert- $C_1$-$C_{10}$ alkyls; specific examples are —CH₃, —C₂H₅, —C₃H₇, i—C₄H₉, and t—C₄H₉. R can be a single hydrocarbon moiety, or a mixture of two or more hydrocarbon moieties.

X is a halogen. F, Cl, Br, and I are all suitable halogens. As with R, X can be a single halogen, or a mixture of two or more halogens.

Z is either a hydrocarbon moiety R or a halogen X. Z can be a mixture of one or more hydrocarbon moieties, halogens, or combinations thereof.

Specific alkyl aluminum halides which may be used are methyl aluminum dichloride, methyl aluminum dibromide, ethyl aluminum dichloride, ethyl aluminum dibromide, ethyl aluminum diiodide, dimethyl aluminum chloride, dimethyl aluminum bromide, diethyl aluminum chloride, diethyl aluminum bromide, di-n-propyl aluminum chloride, and di-n- propyl aluminum bromide, diisobutyl aluminum chloride, and diisobutyl aluminum bromide. Mixtures of these compounds may also be used, as may addition compounds thereof, such as ethyl aluminum sesquichloride and methyl aluminum sesquichloride.

The nonalkylated aluminum halides include AlCl₃, AlBr₃, AlI₃ and AlF₃.

The alkyl aluminum halides are preferred over the nonalkylated aluminum halides as co-catalysts of the invention. While also being suitable, the nonalkylated aluminum halides appear generally to be less effective.

The reasons for this difference are not known at present. While the chemical interaction which takes place in the formation of the catalyst system is not yet fully understood, it is believed that the aluminum halide and ruthenium salt form an alkyl ruthenium species via an initial reaction step.

This step seems to be greatly facilitated where the co-catalyst is an alkyl aluminum halide, due to alkylation of the ruthenium species thereby. In contrast, the nonalkylated aluminum halides may be less effective because, in the absence of the alkyl substituent, the formation of the ruthenium species relies on adventitious alkylation by the olefin and diolefin reactants, and therefore proceeds more slowly.

It is emphasized that the reasoning set forth above is provided only as a possible explanation, without in any way limiting the scope of the invention.

The relative proportions of ruthenium salt and aluminum halide in the catalyst system of the invention can vary over a wide range. Consistent with the above-stated theory regarding formation of the alkyl ruthenium species, the presence of at least one mole of aluminum halide (in the case of alkyl aluminum halides, expressed as mole of available hydrocarbon moiety) per mole of ruthenium salt is preferred, in order to provide for maximum utilization of the ruthenium compound. Regarding this concern, nonalkylated aluminum halides are extremely sensitive to water; alkyl aluminum halides, to both water and oxygen.

Accordingly, to compensate for any deactivation which may result because ambient traces of air and/or water are in the vicinity of the catalyst system, providing a molar excess of alkyl aluminum halide, relative to ruthenium salt, is advisable to maximize utilization of the ruthenium salt. Where such excess is in moderate proportion, no deleterious effect results. Accordingly, while not required, an excess of alkyl aluminum halide over ruthenium salt in the catalyst system is most preferred.

In more specific terms, the ratio of aluminum halide to ruthenium salt may be in the range of 0.5:1 to 100:1; this range is provided as an indication of proportions which are operable in the practice of the invention, and is not intended as a limitation. A preferred range of this ratio of catalyst components is 1:1 to 10:1; most preferably, the range is 1:1 to 4:1.

The proportion of catalyst used in the dimerization reaction can vary widely; among the factors for determining the amount of catalyst used are economic considerations, such as the cost of the catalyst, and the reaction rate required. Preferably, at least about 0.01 gm. ruthenium salt per liter of reaction mixture, and not more than about 10 gm. ruthenium salt per liter of reaction mixture, is used.

An inert solvent is utilized in the catalyst system and dimerization reaction of this invention. Suitable solvents include those with boiling points far removed from the boiling points of the codimerization reaction products. The solvents' boiling points may be either higher or lower than the reaction products' boiling points; preferably, the solvents' boiling points are much higher. This disparity permits easy separation of reaction products from the reaction mixture.

Weakly coordinating solvents are preferred. Specific examples include diethyl ether, dibutyl ether, acetonitrile, and tetrahydrofuran.

Particularly preferred weakly coordinating solvents are the glymes, i.e., the ethylene glycol methyl ethers, having the formula:

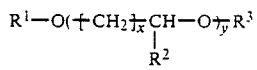

$$R^1-O(-CH_2)_x CH-O)_y R^3$$
$$\quad\quad\quad\quad\quad\quad |$$
$$\quad\quad\quad\quad\quad\quad R^2$$

with $R^1$ and $R^3$ being the same or different, each being a $C_1$ or greater alkyl moiety; $R^2$ being hydrogen or a $C_1$ or greater alkyl moiety; x being 0 or greater; and y being 1 or greater. Specific examples are ethylene glycol dimethyl ether, ethylene glycol diethyl ether, and diethylene glycol dimethyl ether.

Ethylene glycol dimethyl ether and higher homologs thereof are especially preferred; such higher homologs include those ethers characterized by higher glycol oligomers—such as diethylene glycol, triethylene glycol, and higher—in the glycol substituent, as well as those ethers characterized by higher alkyls—such as ethyl, propyl, and higher—as the terminal substituents.

Noncoordinating solvents, including hydrocarbon solvents, such as toluene, may also be used. However, if the catalyst system of the invention is not otherwise provided with a coordinating element or group, e.g., supplied by a neutral coordinating ligand, the trans to cis ratio of the resulting 1,4-diene product will be lower. Accordingly, while noncoordinating solvents are still suitable for the catalyst system of the invention where coordination is not otherwise provided, in such instances they are less preferred.

As earlier discussed with respect to the apparent greater effectiveness of alkyl aluminum halides over nonalkylated aluminum halides, it is not completely understood why the presence of coordinating groups or elements (e.g., neutral coordinating ligands or weakly coordinating solvents) in the catalyst system of the invention seems to have the beneficial effect of increasing the ratio of trans to cis product. It is believed that the coordinating group or element provides this result by complexing with the ruthenium catalyst to form a sterically demanding catalyst environment which favors the formation of the trans 1,4-diene.

The effect of coordinating groups is particularly apparent where the solvent of the catalyst system is a noncoordinating solvent; as discussed above, use of noncoordinating solvents will still result in 1,4-diene product, but with a lower trans to cis ratio than where a weakly coordinating solvent is used.

However, with this same noncoordinating solvent, higher trans to cis ratios will be obtained where a coordination element or group is provided to the catalyst system from some other source, e.g., in the form of a neutral coordinating ligand; as earlier discussed, this ligand may be incorporated as part of the ruthenium catalyst, or added independently to the catalyst system of the invention. A particular combination of solvent and ligand for which this characteristic is demonstrated are toluene and triphenyl phosphine.

While both neutral coordinating ligands and weakly coordinating solvents increase the trans selectivity, it is noted that these ligands are stronger bases than the weakly coordinating solvents, and therefore coordinate more strongly with the ruthenium catalysts. With at least certain of the neutral coordinating ligands, such activity will result in an even higher trans to cis ratio of diene product than is provided by the weakly coordinating solvents.

However, this stronger coordination also has the effect of slowing catalytic activity. Accordingly, the presence of a neutral coordinating ligand in the catalyst system of the invention will lower the diene yield, even if trans selectivity is increased.

For this reason, though neutral coordinating ligands may be present in the catalyst system of the invention, with or without weakly coordinating solvents, it is preferred that the catalyst system instead include such solvents, without these ligands. The weakly coordinating solvents are advantageous in providing coordinating activity which is sufficient to increase trans selectivity, but not so great as to inhibit the yield of 1,4-diene.

Reaction conditions suitable for conducting the 1,4-diene synthesis of the invention may vary broadly. The dimerization can take place within broad ranges of temperature and pressure.

A suitable temperature range for the codimerization reaction is about 25°–250° C. At temperatures below about 50° C., the codimerization rate may be too slow for operating convenience. The preferred temperature range is about 50°–170° C.; about 65°–160° C. is most preferred, this range being particularly suited for practical operations, and for providing good reaction rates.

As to pressure, the codimerization reaction may be conducted within a range of about 1 atmosphere absolute to about 200 atmospheres.

The reaction is allowed to proceed until the desired level of conversion is achieved.

The codimerization of alpha-monoolefin and conjugated diene can be conducted as a batch reaction, as a continuous reaction, or as a semi-continuous reaction. It is understood that the scope of this invention includes any suitable type of reaction method which will facilitate the requisite codimerization; the 1,4-diene synthesis of the invention is not limited to these three types of reactions, which are provided herein as particular, non-limiting examples.

The codimerization reaction is preferably conducted in an environment substantially free of air and water. With reference to air, the component of primary concern is oxygen; accordingly, in providing a reaction environment substantially free of air, it is particularly significant that oxygen be essentially absent.

A codimerization reaction environment substantially free of air and water can be provided by any suitable means. One appropriate means is by blanketing the reaction process with nitrogen gas.

Where the synthesis is conducted as a batch reaction, the reactor can be charged with a solution of ruthenium salt and aluminum halide, dissolved in an inert solvent. The conjugated diolefin reactant, if in liquid form, may also be present in this solution.

The batch reactor is then pressurized with the alpha-monoolefin reactant; The codimerization reaction may be conducted with or without the addition of additional heat. Ethylene can be maintained at a practically constant pressure over the solution; the reaction is allowed to proceed until consumption of ethylene ceases, or to the desired degree of completion.

A suitable batch reaction may also be conducted with introduction of both the alpha-monoolefin and the conjugated diene into the reactor to establish a suitable value of the ratio, before the reaction is initiated; thereafter, additional alpha-monoolefin is fed into the reactor during the course of the reaction, until the desired conversion of the conjugated diene to the 1,4-diene is obtained. One or both of the reactants can be charged to the reaction vessel, continuously or intermittently, during the reaction.

Where appropriate, heat can be applied to the solution prior to pressurization with the alpha-monoolefin. Where such prepressurization heating is employed, the solution is preferably preheated to reaction temperature before pressurization.

Where a continuous reaction is used for the 1,4-diene synthesis, any reactor or combination of reactors suitable for conducting continuous reaction may be employed; for example, a single, elongated reactor, or a series of continuous stirred tank reactors, are suitable. The dimerization process can be initiated by introduction of the requisite components through the inlet of an elongated reactor, or a series of continuous stirred tank reactors. The components are preferably introduced at a rate which provides that the synthesis reaction will be substantially completed by the time the reaction mixture reaches the outlet of the reactor, where a single reactor is used, or the final reactor stage, where multiple reactors are employed.

The dimerization may be conducted as a semi-continuous reaction in a series of tank reactors. Using this type of reaction, the synthesis components are metered into the tank reactor series at the rate appropriate for maintaining the reactor liquid level.

Either continuous or semi-continuous reaction may be provided by altering, during the course of the dimerization reaction, one or more of any of the reaction conditions and concentrations of synthesis components (i.e., alpha-monoolefin, conjugated diolefin, ruthenium salt, aluminum halide, and solvent).

Spent reaction mixture from the dimerization process is flashed to remove unreacted alpha-monoolefin and conjugated diolefin, and 1,4-diene product is recovered by fractionation. What remains after flashing and fractionation is essentially ruthenium salt, aluminum halide, and the solvent in which they are dissolved. This solution may be recycled to the dimerization reaction, i.e., returned to the batch reactor, to the inlet of the single continuous reactor, or to the first stage of the continuous reactor series.

Various mechanisms occurring during the codimerization process may serve to deactivate the ruthenium salt, i.e., convert it to a state other than the $+3$ oxidation state.

For example, as previously discussed, the codimerization process is preferably conducted in an environment free, or substantially free, of ambient air and moisture, i.e., water; however, the presence of ambient air or moisture may oxidize the ruthenium salt to an oxidation state higher than $+3$. As another hazard, reducing agents in the reaction mixture, e.g., the aluminum halide and the olefin reactants, may lower the oxidation state of the ruthenium salt below $+3$.

Accordingly, it is advantageous to employ a means for restoring the ruthenium salt to the desired $+3$ oxidation state. This objective may be accomplished by any suitable means.

As one method, after flashing and fractionation, as previously discussed, the solvent is distilled to obtain a residue, including both the ruthenium salt and the aluminum halide. Oxidation or reduction of the spent ruthenium catalyst is then effected with conventional oxidizing or reducing agents, as may be required by the circumstances, to restore the $+3$ oxidation state: i.e., where deactivation is the result of oxidation, a reducing agent is employed; if the cause of deactivation is reduction, then the means for providing reactivation is an oxidizing agent.

Where the reactivator is an oxidizing agent, and the co-catalyst is an alkyl aluminum halide, the co-catalyst will also be oxidized; however, though effecting reactivation of the ruthenium catalyst, oxidation also deactivates the alkyl aluminum halide. In this instance, accordingly, additional alkyl aluminum halide co-catalyst should be added as well as the oxidizing reactivator.

Ruthenium thus reactivated may then be used again in the codimerization process, in any suitable manner. It may be re-added to the post-flashing and fractionation solution from which it was removed, prior to the recycling of this solution to the reactor or reactors. It may be otherwise used in the preparation of a fresh catalyst system for the codimerization reaction, or for charging the reactor inlet or inlets, where the reaction is specifically conducted by continuous or semi-continuous process.

The 1,4-diene product obtained from the spent reaction mixture may be subjected to additional fractionation to remove impurities, such as traces of unreacted alpha-monoolefin and conjugated diene.

The invention is illustrated by the following representative Examples. All of these were conducted in the substantial absence of oxygen and moisture, and with anhydrous solvents.

PROCEDURE FOR EXAMPLES 1-19

The following procedure was performed in practicing Examples 1-19. In each of Examples 1-19, the alpha-monoolefin and conjugated diolefin reactants are ethylene and 1,3-butadiene, respectively.

The ruthenium catalyst was weighed, then loaded into a pyrex glass liner containing a teflon coated stir bar. The loading was conducted under a nitrogen atmosphere in a controlled atmosphere Dry Box.

Solvent was then added to the pyrex glass liner via syringe, also under this inert atmosphere. The resulting solution was magnetically stirred until the ruthenium catalyst was dissolved. After completion of the stirring, alkyl aluminum halide co-catalyst was added, also via syringe under the inert atmosphere.

The liner, containing the reaction mixture as provided above, was loaded into a 120 cc. stainless steel pressure vessel. After loading, the pressure vessel was sealed, then removed from the inert atmosphere.

The sealed pressure vessel was placed in a stirring/heating manifold. The vent line, as well as butadiene and ethylene reactant charge lines, were all purged with nitrogen for approximately five minutes, then connected.

Liquid butadiene was added to the pressure vessel by pressurizing with nitrogen, and a 2800 Kpa atmosphere of ethylene was charged to the pressure vessel. The vessel was kept at a constant pressure during the course of the reaction.

The reaction mixture was stirred at a rate of 900 RPM, and the mixture was heated to the reaction temperature. The reaction was conducted for a specified period of time between approximately 2.5 and 16.5 hours.

Following the reaction period, the pressure vessel was cooled to ambient temperature, the pressure in the vessel was vented, and the vessel was dismantled. The reaction mixture inside was then analyzed by gas chromatography, using a weighed amount of heptane added after the reaction; the heptane served as an internal standard to determine both the extent of codimerization of the reactants, and the isomer ratio.

EXAMPLE 1

| butadiene | ruthenium salt |
|---|---|
| 20 ml. | 112 mg. Ru(acetylacetonate)$_3$ |
| aluminum halide | solvent |
| 0.2 ml. of 1.8M Et$_2$AlCl | 35 ml. ethylene glycol dimethyl ether |
| reaction temp. | reaction time | total yield of 1,4-diene |
| 70° C. | 4.0 hrs. | 0.88 gm. |
| | trans/cis ratio of 1,4-diene | |
| | 11.40 | |

EXAMPLE 2

| butadiene | ruthenium salt |
|---|---|
| 15 ml. | 116 mg. Ru(acetylacetonate)$_3$ |
| aluminum halide | solvent |
| 0.08 ml. of 1.8M Et$_2$AlCl | 35 ml. ethylene glycol dimethyl ether |
| reaction temp. | reaction time | total yield of 1,4-diene |
| 70° C. | 3.03 hrs. | 0.04 gm. |
| | trans/cis ratio of 1,4-diene | |
| | 10.28 | |

EXAMPLE 3

| butadiene | ruthenium salt |
|---|---|
| 15 ml. | 114 mg. Ru(acetylacetonate)$_3$ |
| aluminum halide | |
| 0.2 ml. of 1.8M Et$_2$AlCl | |
| solvent | |
| 35.0 ml. diethylene glycol dimethyl ether | |
| reaction temp. | reaction time | total yield of 1,4-diene |
| 70° C. | 3.02 hrs. | 0.61 gm. |
| | trans/cis ratio of 1,4-diene | |
| | 7.24 | |

EXAMPLE 4

| butadiene | ruthenium salt |
|---|---|
| 15 ml. | 114 mg. Ru(acetylacetonate)$_3$ |
| aluminum halide | |
| 0.17 ml. of 1.8M Et$_3$Al$_2$Cl$_3$ | |
| solvent | |
| 35 ml. ethylene glycol dimethyl ether | |
| reaction temp. | reaction time | total yield of 1,4-diene |
| 70° C. | 3.05 hrs. | 1.10 gm. |
| | trans/cis ratio of 1,4-diene | |
| | 13.70 | |

EXAMPLE 5

| butadiene | ruthenium salt |
|---|---|
| 15 ml. | 112 mg. Ru(acetylacetonate)$_3$ |
| aluminum halide | |
| 0.17 ml. of 1.8M Et$_3$Al$_2$Cl$_3$ | |
| solvent | |
| 35 ml. ethylene glycol dimethyl ether | |
| reaction temp. | reaction time | total yield of 1,4-diene |
| 80° C. | 3.0 hrs. | 1.22 gm. |
| | trans/cis ratio of 1,4-diene | |
| | 19.27 | |

EXAMPLE 6

| butadiene | ruthenium salt |
|---|---|
| 15 ml. | 112 mg. Ru(acetylacetonate)$_3$ |
| aluminum halide | |
| 0.33 ml. of 1.8M Et$_3$Al$_2$Cl$_3$ | |
| solvent | |
| 35 ml. glycol dimethyl ether | |
| reaction temp. | reaction time | total yield of 1,4-diene |
| 70° C. | 16.5 hrs. | 2.78 gm. |
| | trans/cis ratio of 1,4-diene | |
| | 13.82 | |

EXAMPLE 7

| butadiene | ruthenium salt |
|---|---|
| 15 ml. | 113 mg. Ru(acetylacetonate)$_3$ |
| aluminum halide | |
| 0.17 ml. of 1.8M Et$_3$Al$_2$Cl$_3$ | |
| 44 mg. AlCl$_3$ | |
| solvent | |
| 35 ml. ethylene glycol dimethyl ether | |
| reaction temp. | reaction time | total yield of 1,4-diene |
| 70° C. | 3.08 hrs. | 1.11 gm. |
| | trans/cis ratio of 1,4-diene | |
| | 16.46 | |

Example 7 demonstrates that favorable 1,4-diene trans/cis ratios and total yields are obtained where both a nonalkylated and an alkyl aluminum halide are included as co-catalysts for the catalyst system of the invention.

EXAMPLE 8

| butadiene | ruthenium salt |
|---|---|
| 15 ml. | 115 mg. Ru(acetylacetonate)$_3$ |
| aluminum halide | |
| 0.17 ml. of 1.8M Et$_3$Al$_2$Cl$_3$ | |
| solvent | |
| 35 ml. acetonitrile | |
| reaction temp. | reaction time | total yield of 1,4-diene |
| 70° C. | 3.0 hrs. | 0.191 gm. |
| | trans/cis ratio of 1,4-diene | |
| | 13.56 | |

EXAMPLE 9

| butadiene | ruthenium salt |
|---|---|
| 15 ml. | 112 mg. Ru(acetylacetonate)$_3$ |
| aluminum halide | solvent |
| 0.17 ml. of 1.8M Et$_3$Al$_2$Cl$_3$ | 35 ml. tetrahydrofuran |
| reaction temp. | reaction time | total yield of 1,4-diene |
| 70° C. | 3.0 hrs. | 0.172 gm. |
| | trans/cis ratio of 1,4-diene | |
| | 8.45 | |

EXAMPLE 10

| butadiene | ruthenium salt |
|---|---|
| 15 ml. | 211 mg. Ru(hexafluoroacetylacetonate)$_3$ |
| | aluminum halide |
| | 0.30 ml. of 1.8M Et$_3$Al$_2$Cl$_3$ |
| | solvent |
| | 35 ml. ethylene glycol dimethyl ether |
| reaction temp. | reaction time | total yield of 1,4-diene |
| 70° C. | 3.0 hrs. | 0.004 gm. |
| | trans/cis ratio of 1,4-diene |
| | 3.83 |

EXAMPLE 11

| butadiene | ruthenium salt |
|---|---|
| 15 ml. | 165 mg. Ru(benzoylacetonate)$_3$ |
| | aluminum halide |
| | 0.30 ml. of 1.8M Et$_3$Al$_2$Cl$_3$ |
| | solvent |
| | 35 ml. ethylene glycol dimethyl ether |
| reaction temp. | reaction time | total yield of 1,4-diene |
| 70° C. | 3.0 hrs. | 0.244 gm. |
| | trans/cis ratio of 1,4-diene |
| | 12.28 |

EXAMPLE 12

| butadiene | ruthenium salt |
|---|---|
| 15 ml. | 112 mg. Ru(acetylacetonate)$_3$ |
| aluminum halide | solvent |
| 49 mg. AlCl$_3$ | 30 ml. ethylene glycol dimethyl ether |
| reaction temp. | reaction time | total yield of 1,4-diene |
| 70° C. | 3.0 hrs. | 0.089 gm. |
| | trans/cis ratio of 1,4-diene |
| | 3.22 |

EXAMPLE 13

| butadiene | ruthenium salt |
|---|---|
| 15 ml. | 112 mg. Ru(acetylacetonate)$_3$ |
| aluminum halide | alcohol |
| 48 mg. AlCl$_3$ | 3.0 ml. EtOH |
| solvent | reaction temp. |
| 35 ml. ethylene glycol dimethyl ether | 70° C. |
| reaction time | total yield of 1,4-diene |
| 3.0 hrs. | 0.176 gm. |
| trans/cis ratio of 1,4-diene |
| 5.72 |

EXAMPLE 14

| butadiene | ruthenium salt |
|---|---|
| 15 ml. | 112 mg. Ru(acetylacetonate)$_3$ |
| aluminum halide | solvent |
| 0.2 ml. of 1.8M Et$_2$AlCl | 35 ml. toluene |
| reaction temp. | reaction time | total yield of 1,4-diene |
| 70° C. | 2.62 hrs. | 0.515 gm. |
| | trans/cis ratio of 1,4-diene |
| | 3.72 |

EXAMPLE 15

| butadiene | ruthenium salt |
|---|---|
| 15 ml. | 114 mg. Ru(acetylacetonate)$_3$ |
| aluminum halide | neutral coordinating ligand |
| 0.2 ml. of 1.8M Et$_2$AlCl | 78 mg. P($\phi_3$) |
| solvent | reaction temp. | reaction time |
| 35 ml. toluene | 70° C. | 2.62 |
| total yield of 1,4-diene | trans/cis ratio of 1,4-diene |
| 0.08 gm. | 8.43 |

Examples 14 and 15 demonstrate the effect of a neutral coordinating ligand on the activity of the catalyst system of the invention. Except for the insignificant difference in amount of ruthenium salt, the reaction conditions and components of Examples 14 and 15 are identical, except for the presence, in the catalyst system of Example 15, of triphenyl phosphine. The stronger coordination provided by this neutral coordinating ligand, as compared to the weakly coordinating diethylene glycol dimethyl ether solvent, beneficially increases the trans/cis ratio of the 1,4-diene product, but lowers the yield for the same reaction time.

EXAMPLE 16

| butadiene | ruthenium salt |
|---|---|
| 15 ml. | 113 mg. Ru(acetylacetonate)$_3$ |
| aluminum halide | neutral coordinating ligand |
| 0.2 ml. of 1.8M Et$_2$AlCl | 93 mg. (Bu$_3$PO) |
| solvent | reaction temp. |
| 35 ml. ethylene glycol dimethyl ether | 70° C. |
| reaction time | total yield of 1,4-diene |
| 3.38 hrs. | 0.0021 gm. trans isomer |
| trans/cis ratio of 1,4-diene |
| infinity; no cis isomer produced |

Example 16 is consistent with Example 15 in showing the effect of a neutral coordinating ligand. The coordination provided by tri-n-butyl phosphine oxide is so strong as to prevent the formation of cis isomer, while correspondingly lowering the total 1,4-diene yield even further.

In the catalyst systems of the following Examples, Examples 17–19, the co-catalysts are not aluminum halides.

EXAMPLE 17

| butadiene | ruthenium salt |
|---|---|
| 15 ml. | 116 mg. Ru(acetylacetonate)$_3$ |
| co-catalyst | solvent |
| 0.23 ml. Et$_2$AlOEt | 35 ml. ethylene glycol dimethyl ether |
| reaction temp. | reaction time |
| 70° C. | 3.05 hrs. |
| total yield of 1,4-diene | trans/cis ratio of 1,4-diene |
| — | — |

Like the alkyl aluminum halides, the co-catalyst used in Example 17 is also both an alkylating agent and a Lewis acid. However, the attempted dimerization utilizing this co-catalyst produces no 1,4-dienes.

EXAMPLE 18

| butadiene | ruthenium salt |
|---|---|
| 15 ml. | 112 mg. Ru(acetylacetonate)$_3$ |
| co-catalyst | solvent |
| 25 mg. NaBH$_4$ | 35 ml. ethylene glycol dimethyl ether |
| 61 mg. BF$_3$.OEt$_2$ | |
| reaction temp. | reaction time |
| 70° C. | 3.05 hrs. |
| total yield of 1,4-diene | trans/cis ratio of 1,4-diene |

-continued

| | |
|---|---|
| 0.023 gm. cis isomer | no trans isomer produced |

The catalyst system of Example 18 includes two co-catalysts. One of these, NaBH$_4$ is a Lewis acid, and the other, BF$_3$.OEt$_2$, is both a Lewis acid and an alkylating agent. However, the resulting 1,4-diene includes no trans isomer.

EXAMPLE 19

| butadiene | ruthenium salt |
|---|---|
| 15 ml. | 112 mg. Ru(acetylacetonate)$_3$ |
| co-catalyst | solvent |
| 0.16 ml. Et$_3$Al | 35 ml. ethylene glycol dimethyl ether |
| reaction temp. | reaction time |
| 70° C. | 3.08 hrs. |
| total yield of 1,4-diene | trans/cis ratio of 1,4-diene |
| 0.0032 gm. | 0.20 |

The Et$_3$Al co-catalyst used in the catalyst system of Example 19 is both an alkylating agent and a strong Lewis acid. However, the preponderance of the 1,4-diene product comprises the cis-isomer.

PROCEDURE FOR EXAMPLES 20-24

The following procedure was performed in practicing Examples 20-24. In each of these Examples, the alpha-monoolefin and conjugated diolefin reactants are propylene and isoprene, respectively.

The loading and mixing of the ruthenium catalyst and solvent was accomplished in the same manner as utilized for the procedure of Examples 1-19. Thereafter, still under the inert atmosphere, isoprene was added, like the solvent, via syringe.

Aluminum halide co-catalyst was added to the reaction mixture after the indicated insertion of solution. As in the procedure for Examples 1-19, the liner was placed in the pressure vessel, which was then sealed, removed from the inert atmosphere, and placed in a stirring/heating manifold. Vent and reactant lines were purged and connected; however, in contrast to the procedure for Examples 1-19, the only reactant line utilized was for propylene.

Propylene was charged into the reactor through this reactant line using 2000 Kpa nitrogen head pressure. The reaction mixture was stirred at 900 RPM, and heated to 110° C.

After the reaction period, the same steps of cooling, venting, dismantling, and analysis were used as in the procedure for Examples 1-19.

EXAMPLE 20

| propylene | isoprene |
|---|---|
| 15.05 gm. | 7.0 ml. |
| ruthenium salt | |
| 113 mg. Ru(acetylacetonate)$_3$ | |
| aluminum halide | |
| 0.17 ml, of 1.8M Et$_3$Al$_2$Cl$_3$ | |
| solvent | reaction temperature |
| 25.0 ml. ethylene glycol dimethyl ether | 110° C. |
| reaction time | total yield of 1,4-dienes |
| 3.0 hrs. | 0.173 gm. |

EXAMPLE 21

| propylene | isoprene |
|---|---|
| 15.15 ml. | 7.0 ml. |
| ruthenium salt | |
| 225 mg. Ru(acetylacetonate)$_3$ | |
| aluminum halide | |
| 0.17 ml. of 1.8M Et$_3$Al$_2$Cl$_3$ | |
| solvent | reaction temperature |
| 25.0 ml. ethylene glycol dimethyl ether | 110° C. |
| reaction time | total yield of 1,4-dienes |
| 3.07 | 1.63 gm. |

EXAMPLE 22

| propylene | isoprene |
|---|---|
| 10 gm. | 10 ml. |
| ruthenium salt | |
| 116 mg. Ru(acetylacetonate)$_3$ | |
| aluminum halide | |
| 0.17 ml. of 1.8M Et$_3$Al$_2$Cl$_3$ | |
| solvent | reaction temperature |
| 25.0 ml. ethylene glycol dimethyl ether | 90° C. |
| reaction time | total yield of 1,4-dienes |
| 3.0 | 1.985 gm. |

EXAMPLE 23

| propylene | isoprene |
|---|---|
| 15.21 gm. | 5.0 ml. |
| ruthenium salt | |
| 112 mg. Ru(acetylacetonate)$_3$ | |
| aluminum halide | |
| 0.22 ml. of 1.8M diisobutyl aluminum chloride | |
| solvent | reaction temperature |
| 25.0 ml. ethylene glycol dimethyl ether | 70° C. |
| reaction time | total yield of 1,4-dienes |
| 3.0 | 0.1264 gm. |

EXAMPLE 24

| propylene | isoprene |
|---|---|
| 15.22 gm. | 5.0 ml. |
| ruthenium salt | |
| 0.089 gm. RuCl$_3$.3H$_2$O | |
| aluminum halide | |
| 0.28 ml. of 1.8M Et$_3$Al$_2$Cl$_3$ | |
| solvent | reaction temperature |
| 25.0 ml. ethylene glycol dimethyl ether | 70° C. |
| reaction time | total yield of 1,4-dienes |
| 3.0 | 0.13 gm. |

Finally, although the invention has, as has been noted above, been described with reference to particular means, materials and embodiments, it should be noted that the invention is not limited to the particulars disclosed, and extends to all equivalents within the scope of the claims.

What is claimed is:

1. A process for preparing a 1,4-diene, said process comprising reacting an alpha-monoolefin and a conjugated diolefin in the presence of a catalyst system comprising a ruthenium salt and an aluminum halide.

2. The process as defined by claim 1 wherein the ruthenium salt is selected from the group consisting of ruthenium (III) salts and ruthenium salts which can be converted to the +3 oxidation state.

3. The process as defined by claim 2 wherein the ruthenium salt is a ruthenium (III) salt.

4. The process as defined by claim 4 wherein the ruthenium(III) salt is selected from the group consisting of RuBr$_3$, RuCl$_3$, RuI$_3$, RuBr$_3$XH$_2$O, RuCl$_3$XH$_2$O, RuI$_3$XH$_2$O, Ru(acetylacetonate)$_3$, Ru hexa(fluoroacetylacetonate)$_3$, Ru(benzoylacetonate)$_3$, RuCl$_3$(NH$_3$)$_5$, RuCl$_3$(NH$_3$)$_6$, RuCl$_3$NO, (NH$_4$)$_2$[RuCl$_5$], K$_2$[RuCl$_5$], RuNO(NO$_3$)$_3$, and K$_3$Ru(C$_2$O$_4$)$_3$.

5. The process as defined by claim 4 wherein the ruthenium(III) salt is selected from the group consisting of Ru(acetylacetonate)$_3$ and RuCl$_3$XH$_2$O.

6. The process as defined by claim 5 wherein the aluminum halide is an alkyl aluminum halide selected from the group consisting of diethyl aluminum chloride and ethyl aluminum sesquichloride.

7. The process as defined by claim 6 wherein the catalyst system further comprises a solvent selected from the group consisting of ethylene glycol dimethyl ether and diethylene glycol dimethyl ether.

8. The process as defined by claim 6 wherein the catalyst system further comprises n-tri-butyl phosphine oxide.

9. The process as defined by claim 1 wherein the aluminum halide is an alkyl aluminum halide.

10. The process as defined by claim 9 wherein the catalyst system further comprises a nonalkylated aluminum halide selected from the group consisting of AlCl$_3$, AlBr$_3$, AlI$_3$, and AlF$_3$.

11. The process as defined by claim 10 wherein the alkyl aluminum halide is ethyl aluminum sesquichloride, and the nonalkylated aluminum halide is AlCl$_3$.

12. The process as defined by claim 9 wherein the alkyl aluminum halide has the general formula:

RAlXZ wherein
R is a selected from the group consisting of C$_1$-C$_{10}$ hydrocarbons, and mixtures thereof;
X is a halogen selected from the group consisting of F, Cl, Br, I, and mixtures thereof; and
Z is selected from the group consisting of R and X.

13. The process as defined by claim 9 wherein the alkyl aluminum halide is selected from the group consisting of methyl aluminum dichloride, methyl aluminum dibromide, ethyl aluminum dichloride, ethyl aluminum dibromide, ethyl aluminum diiodide, dimethyl aluminum chloride, dimethyl aluminum bromide, diethyl aluminum chloride, diethyl aluminum bromide, di-n-propyl aluminum chloride, di-n-propyl aluminum bromide, mixtures thereof, and additional compounds thereof.

14. The process as defined by claim 9 wherein the alkyl aluminum halide is selected from the group consisting of ethyl aluminum sesquichloride and methyl aluminum sesquichloride.

15. The process as defined by claim 9 wherein the catalyst system comprises at least one mole of alkyl aluminum halide, expressed as mole of available hydrocarbon moiety, per mole of ruthenium salt.

16. The process as defined by claim 15 wherein the catalyst system comprises between about one and about four moles of alkyl aluminum halide, expressed as moles of available hydrocarbon moiety, per mole of ruthenium salt.

17. The process defined by claim 1 wherein the aluminum halide is at least one nonalkylated aluminum halide selected from the group consisting of AlCl$_3$, AlBr$_3$, AlI$_3$, and AlF$_3$.

18. The process as defined by claim 17 wherein the aluminum halide is AlCl$_3$.

19. The process as defined by claim 1 wherein the catalyst system further comprises a solvent.

20. The process as defined by claim 19 wherein the solvent has a boiling point higher than the reaction products obtained from a codimerization reaction utilizing said catalyst system.

21. The process as defined by claim 19 wherein the solvent is a weakly coordinating solvent.

22. The process as defined by claim 21 wherein the weakly coordinating solvent is selected from the group consisting of diethyl ether, dibutyl ether, acetonitrile, tetrahydrofuran, ethylene glycol dimethyl ether, ethylene glycol diethyl ether, and diethylene glycol dimethyl ether.

23. The process as defined by claim 21 wherein the weakly coordinating ether solvent has the formula

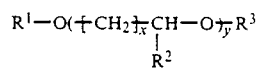

wherein
R$^1$ is an alkyl group having at least one carbon atom;
R$^2$ is selected from the group consisting of hydrogen and alkyl groups having at least two carbon atoms;
R$^3$ is an alkyl group having at least one carbon atom, and is either the same as or different from R$^1$;
x is 0 or greater; and
y is 1 or greater.

24. The process as defined by claim 23 wherein the weakly coordinating solvent is ethylene glycol dimethyl ether.

25. The process as defined by claim 19 wherein the solvent is a noncoordinating solvent.

26. The process as defined by claim 25 wherein the noncoordinating solvent is toluene.

27. The process as defined by claim 25 wherein the catalyst system further comprises a neutral coordinating ligand.

28. The process as defined by claim 1 wherein the catalyst system further comprises a neutral coordinating ligand.

29. The process as defined by claim 28 wherein said neutral coordinating ligand is selected from the group consisting of nitriles, phosphines, carbonyls, arsines, stibines, and mixtures thereof.

30. The process as defined by claim 29 wherein the neutral coordinating ligand has a formula selected from the group consisting of (R$^4$)$_3$M and (R$^4$)$_3$MO, wherein:
R$^4$ is a hydrocarbon moiety selected from the group consisting of methyl, ethyl, propyl, n-butyl, isobutyl, t-butyl, and phenyl; and
M is selected from the group consisting of P, As, and Sb.

31. The process as defined by claim 30 wherein the neutral coordinating ligand is selected from the group consisting of triethyl phosphine and tri-n-butyl phosphine oxide.

32. The process as defined by claim 1 wherein the ruthenium salt is a ruthenium salt which can be converted to the +3 oxidation state, the ruthenium salt, prior to conversion, having an oxidation state greater than +3.

33. The process as defined by claim 32 wherein the ruthenium salt having an oxidation state greater than +3 is selected from the group consisting of $RuO_4$, $NaRuCl_5$, $NaRuBr_5$, $(NH_4)_2RuCl_6$, $KRuO_4$, $K_2RuO_4$, $NaRuO_4$, and $RuO_2$.

34. The process as defined by claim 33 wherein the catalyst system further comprises a solvent.

35. The process as defined by claim 34 wherein the solvent is a weakly coordinating solvent.

36. A process for preparing a 1.4 diene, said process comprising:
  (a) reducing a ruthenium salt, having an oxidation state greater than +3, to the +3 oxidation state;
  (b) forming a catalyst system comprising an alkyl aluminum halide, and the ruthenium salt in the +3 oxidation state; and
  (c) reacting an alpha-monoolefin and a conjugated diolefin in the presence of said catalyst system.

37. The process as defined by claim 36 wherein step (a) comprises reacting the ruthenium salt with a reducing agent.

38. The process as defined by claim 37 wherein the ruthenium salt, having an oxidation state greater than +3, is selected from the group consisting of $RuO_4$, $NaRuCl_5$, $NaRuBr_5$, $(NH_4)_2RuCl_6$, $KRuO_4$, $K_2RuO_4$, $NaRuO_4$, and $RuO_2$.

39. The process as defined by claim 38 wherein step (b) comprises dissolving the ruthenium salt and the alkyl aluminum halide in a solvent.

40. The process as defined by claim 39 wherein the solvent is a weakly coordinating ether solvent.

41. A process for preparing a 1.4 diene, said process comprising:
  (a) oxidizing a ruthenium salt, having an oxidation state less than +3, to the +3 oxidation state;
  (b) forming a catalyst system comprising an alkyl aluminum halide, and the ruthenium salt in the +3 oxidation state; and
  (c) reacting an alpha-monoolefin and a conjugated diolefin in the presence of said catalyst system.

42. The process as defined by claim 41 wherein step (a) comprises reacting the ruthenium salt with an oxidizing agent.

43. The process as defined by claim 42 wherein the ruthenium salt, having an oxidation state less than +3, is selected from the group consisting of $K_4[Ru(CN)_6]$, $K_2[Ru(CO)_2Cl_4]$, $K[Ru(CO)_3Cl_3]$, $Ru(H_2NCH_2CH_2NH_2)_3Cl_2$, $Ru(P\phi_3)_2(CO)_2Cl_2$, $Ru(P\phi_3)_2(CO)_3$, $Ru(P\phi_3)_3Cl_2$, $Ru(NH_3)_3Cl_2$ $HRu(P\phi_3)_3(CO)Cl$, $H_2Ru(P\phi_3)_3(CO)$, $HRu(P\phi_3)_3Cl$, $H_2Ru(P\phi_3)_4Ru(NH_3)_6Cl_2$, and $Ru_3(CO)_{12}$.

44. The process as defined by claim 43 wherein step (B) comprises dissolving said ruthenium salt and said alkyl aluminum halide in a solvent.

45. The process as defined by claim 44 wherein said solvent is a weakly coordinating ether solvent.

* * * * *